United States Patent [19]
Abele et al.

[11] Patent Number: 5,385,152
[45] Date of Patent: Jan. 31, 1995

[54] GUIDEWIRE FOR CROSSING OCCLUSIONS IN BLOOD VESSELS

[75] Inventors: John E. Abele, Concord, Mass.; Kevin R. Heath, Providence, R.I.; Mark S. Landman, Sharon; Paul D. McLaughlin, Scituate, both of Mass.

[73] Assignee: Boston Scientific Corporation, Watertown, Mass.

[21] Appl. No.: 62,058

[22] Filed: May 14, 1993

Related U.S. Application Data

[63] Continuation-in-part of Ser. No. 611,296, Nov. 9, 1990, abandoned.

[51] Int. Cl.$^6$ .............................................. A61M 23/00
[52] U.S. Cl. ................................... 128/772; 606/191; 128/657
[58] Field of Search .............................. 128/656–658, 128/772; 604/164, 170, 280, 282; 606/191

[56] References Cited

U.S. PATENT DOCUMENTS

| | | | |
|---|---|---|---|
| 1,878,671 | 9/1932 | Cantor | 604/170 |
| 2,022,065 | 11/1935 | Wappler | 174/89 |
| 2,047,535 | 7/1936 | Wappler | 128/303 |
| 3,196,876 | 7/1965 | Miller | 128/343 |
| 3,516,412 | 6/1970 | Ackerman | 128/418 |
| 3,687,142 | 8/1972 | Leibinzohn | 128/348 |
| 3,867,945 | 2/1975 | Long | 128/349 |
| 3,928,519 | 12/1975 | Kashiyama et al. | 264/40 |
| 3,973,556 | 8/1976 | Fleischhaker et al. | 128/2 |
| 3,999,551 | 12/1976 | Spitz et al. | 128/303 |
| 4,013,079 | 3/1977 | Lindemann et al. | 128/341 |
| 4,195,637 | 4/1980 | Grüntzig et al. | 128/348 |
| 4,306,566 | 12/1981 | Sinko | 128/658 |
| 4,345,602 | 8/1982 | Yoshimura et al. | 128/349 |
| 4,385,635 | 5/1983 | Ruiz | 174/658 |
| 4,388,076 | 6/1983 | Waters | 604/165 |
| 4,531,943 | 7/1985 | Van Tassel et al. | 604/280 |
| 4,538,622 | 9/1985 | Samson et al. | 128/772 |
| 4,554,929 | 11/1985 | Samson et al. | 128/772 |
| 4,619,274 | 10/1986 | Morrison | 128/772 |
| 4,643,194 | 2/1987 | Fogarty | 128/668 |
| 4,665,906 | 5/1987 | Jervis | 128/92 |
| 4,690,175 | 9/1987 | Ouchi et al. | 138/131 |
| 4,748,986 | 6/1988 | Morrison et al. | 128/772 |
| 4,884,579 | 12/1989 | Engelson | 128/772 |
| 4,917,102 | 4/1990 | Miller et al. | 128/772 |
| 4,925,445 | 5/1990 | Sakamoto et al. | 604/95 |
| 4,955,862 | 9/1990 | Sepetka | 604/164 |
| 4,991,602 | 2/1991 | Amplatz et al. | 128/772 |
| 5,003,990 | 4/1991 | Osypka | 128/772 |
| 5,045,061 | 9/1991 | Seifert et al. | 604/96 |
| 5,059,183 | 10/1991 | Semrad | 604/158 |
| 5,095,915 | 3/1992 | Engelson | 128/772 |
| 5,111,829 | 5/1992 | Alvarez de Toledo | 128/772 |
| 5,127,917 | 7/1992 | Niederhauser et al. | 606/191 |
| 5,238,004 | 8/1993 | Sahatjian et al. | 128/772 |

FOREIGN PATENT DOCUMENTS

| | | |
|---|---|---|
| 2017901 | 12/1990 | Canada . |
| 0014424 | 8/1980 | European Pat. Off. . |
| 0141006 | 5/1985 | European Pat. Off. . |
| 0363661 | 4/1990 | European Pat. Off. . |
| 0396074 | 11/1990 | European Pat. Off. . |
| WO85/01444 | 4/1985 | WIPO . |
| WO86/05103 | 9/1986 | WIPO . |
| WO91/19528 | 12/1991 | WIPO . |

OTHER PUBLICATIONS

Meier et al., "Magnum Wire for Balloon Recanalization of Chronic Total Coronary Occlusions," Am. J. Cardiol., 64: 148–154 (Jul. 15, 1989).

(List continued on next page.)

Primary Examiner—John D. Yasko
Assistant Examiner—Adam J. Cermak
Attorney, Agent, or Firm—Fish & Richardson

[57] ABSTRACT

A steerable guidewire for gently penetrating an occlusion within a vessel, with an elongated solid main guidewire body having selected stiffness characteristics along its length to allow the guidewire to be urged through a narrow, tortuous body lumen by application of forces at a proximal end, and an enlarged distal end portion having a diameter larger than portions of the guidewire proximal thereof including a soft polymeric element and a permanently deflected portion to enable steering of the guidewire.

16 Claims, 5 Drawing Sheets

OTHER PUBLICATIONS

Tonnesen et al., "Femoral Artery Recanalization with Percutaneous Angioplasty and Segmentally Enclosed Plasminogen Activator"; May, 1990.

Schneider (Europe) AG, Pfizer Hospital Products Group, "Magnum-Meier TM" (Aug., 1990).

Baim et al., "Coronary Angioplasty for Total Occlusion: Ongoing Problems Despite Improving Results," JACC 15; 857–858 (Mar. 15, 1990).

Ginsburg, "Laser Angioplasty as an Adjunct to Balloon Dilatation," (ch. 36) Endovascular Surgery (Moore et al., eds.) 389–392 (1989).

Lammer et al., "Recanalization of Arteriosclerotic Occlusions: Excimer Laser, ND-YAG Laser; Guide Wire; A Preliminary Report of a Randomized Trial." undated.

Rees, "Treatment of Chronic Coronary Artery Occlusions with an olive tipped guide wire (Magnus) versus Terumo Glidewire,". undated.

Voda, "Angled Tip of the Steerable Guidewire and Its Usefulness in Percutaneous Transluminal Coronary Angioplasty", 1987.

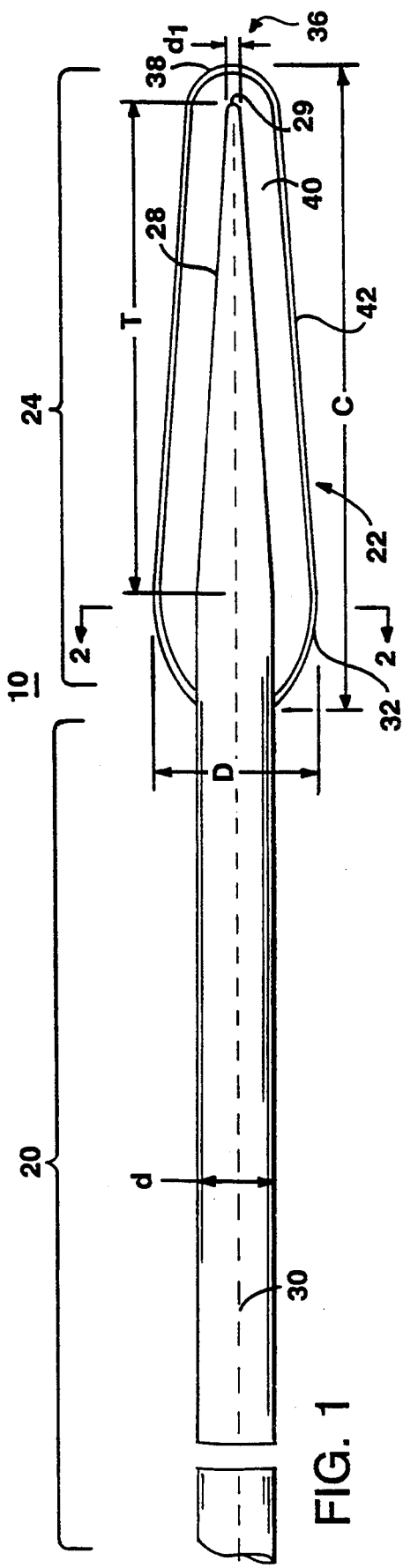
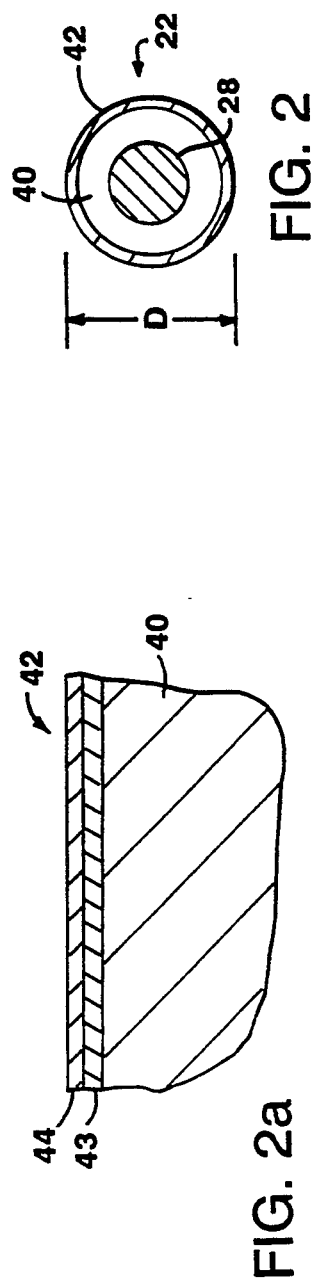

GUIDEWIRE FOR CROSSING OCCLUSIONS IN BLOOD VESSELS

CROSS-REFERENCE TO RELATED APPLICATION

This application is a continuation-in-part of U.S. Ser. No. 07/611,296, filed Nov. 9, 1990, now abandoned, the entire contents of which is hereby incorporated by reference.

BACKGROUND OF THE INVENTION

The invention relates to medical guidewires for narrow passages of a body, and particularly guidewires that are designed to cross an occlusion of a duct or vessel, such as a coronary artery. A physician introduces the distal end of the guidewire into the body, e.g., via a puncture, and manipulates the flexible tip of the guidewire to enter the desired passageway and follow its convolutions to a treatment site. A dilatation catheter or other medical device may then be advanced over the guidewire to the site.

SUMMARY OF THE INVENTION

In one aspect, the invention features a steerable medical guidewire for gently penetrating an occlusion within a vessel. The guidewire has an elongated main guidewire body with selected stiffness characteristics along its length to allow the guidewire to be urged through a narrow, tortuous body lumen by application of forces at a proximal end. The guidewire has a composite enlarged distal end portion formed of an extension of the main guidewire body and a surrounding enlarged soft outer polymeric element. The polymeric element has a substantial thickness compared to corresponding portions of the guidewire body and a lubricious outer surface. The enlarged distal end portion includes a gently deflected region, to enable steering of the guidewire inside the vessel. The deflected region and the stiffness of the guidewire are cooperatively constructed to permit the enlarged distal end portion, including the deflected portion, to gently penetrate the occlusion and form a passage therein.

In another aspect, the invention features a steerable guidewire for gently penetrating an occlusion within a vessel. The guidewire has an elongated solid main guidewire body with selected stiffness characteristics along its length to allow the guidewire to be urged through a narrow, tortuous body lumen by application of forces at a proximal end, and an enlarged distal end portion with a diameter larger than portions of the guidewire proximal thereof, and including a soft polymeric element and a permanently deflected portion to enable steering of the guidewire.

Various embodiments may include one or more of the following features. The deflected portion is formed by at an angle of about 15° to 35° from the axis of the main guidewire body. The angle is formed by a bend located about 0.5 to 0.75 cm from the distal end of the polymeric element. The enlarged distal end portion is a composite of an extension of the main guidewire body and a surrounding enlarged soft outer polymeric element having a diameter larger than the diameter of portions of the main guidewire body proximal of the enlarged distal end portion. The portion of the guidewire body in the distal part of the enlarged distal end portion is of smaller diameter than the portion of the guidewire body in the proximal part of the enlarged distal end portion. The flexibility of the enlarged distal end portion is determined over substantially all of its length predominantly by the respective portions of the guidewire body therewithin. The guidewire is adapted for use in the vascular system and has a wire body with a maximum diameter of about 0.018 inch or less. The enlarged distal end portion has a diameter of about 0.035 inch or less. In at least portions of the enlarged distal end portion, the thickness of the soft polymeric element is about equal to or greater than the radius of the corresponding portion of the wire body. The guidewire body is formed of a solid wire. The guidewire body is nitinol. The distal extremity of the extension of the main guidewire body is about 0.003 to about 0.005 inch diameter. The polymeric element has a substantially cylindrical configuration of substantially constant cross-sectional diameter and a curve at a most distal end. The soft outer polymeric element is formed of a flexible nylon polymer. The exterior surface of the soft outer polymeric element includes a thin hydrophilic coating of a hydrogel polymer. The enlarged distal end portion is about 2 to 3 cm long. The body has an exterior surface that includes a lubricious coating. The invention also includes methods of use of wires such as the above, including, for example, the steps of torquing or rotating the wire to orient the deflected portion in the direction of an arterial branch, urging the wire axially distally into the branch and to the point of an occlusion, and crossing the occlusion.

According to another aspect of the invention, a medical guidewire for penetrating an occlusion within a duct or vessel, such as a small blood vessel, has an elongated main guidewire body of a small, first diameter, which is terminated at its distal end with an enlarged resilient tip portion having a lubricious outer surface shaped and constructed to penetrate the occlusion. The guidewire body is constructed to be relatively flexible in the distal end corresponding to the enlarged tip and to be relatively stiffer in portions proximal thereof for manipulation of the wire from its proximal end to cause the distal tip portion to penetrate the occlusion and form a passage therein.

Preferred embodiments of the invention have one or more of the following features. The guidewire is constructed, after formation of the passage in the occlusion, to be advanced to move the tip portion distally beyond the occlusion while advancing a portion of the small main guidewire body across the occlusion, in position to guide a dilatation catheter into the passage. The enlarged tip portion of the guidewire is about the same maximum size as the outer diameter of the deflated balloon of the dilatation catheter. The guidewire is in combination with a dilatation catheter comprised of a catheter shaft carrying a deflated dilatation balloon. The catheter has an internal lumen sized to slide over the main body of the guidewire. The dilatation catheter is constructed thereupon to be advanced over the guidewire across the occlusion to position the balloon thereof in dilatation position in the passage in the occlusion.

Preferred embodiments also include the following. The guidewire body and enlarged tip are cooperatively constructed such that the distal end of the guidewire corresponding to the enlarged tip has greater flexibility at distal portions, than proximal portions. The distal end corresponding to the enlarged tip has gradually increasing flexibility from proximal to distal portions. The enlarged tip portion is tapered to smaller diameters toward the distal end. The tip portion is formed from a plurality of materials, having varying flexibility. The materials are polymers of varying softness. The guidewire body is tapered to smaller diameters toward the distal end. The enlarged tip is of substantially constant cross-sectional diameter and has a curved portion at its most distal end. The lubricious outer surface of the enlarged tip portion is a lubricious hydrophilic plastic.

Preferred embodiments also include the following. The enlarged tip portion is an integral extension of the main body of the guidewire, that serves as the core of the distal portion; the integral extension tapers distally to a narrower dimension at its end, and the hydrophilic plastic is a coating adhered to the exterior of the tapered extension. The guidewire body has a lubricious coating.

Preferred embodiments also include the following. The guidewire is used in combination with an outer sleeve having a lumen sized to slide over the main body of the guidewire and butt against the proximal end of the enlarged tip portion, the sleeve contributing to the axial stiffness of the combination to enable manipulation through the occlusion, and being removable to enable a catheter thereafter to be slid over the guidewire. The outer diameter of the sleeve corresponds generally to the maximum dimension of the distal tip portion of the guidewire. The proximal end of the outer sleeve is maintained in a fixed position relative to the proximal end of the guidewire. The guidewire body comprises a solid core of material. The guidewire is a superelastic or linear elastic alloy. The guidewire is adapted for use in small blood vessels and the main guidewire body has an outer diameter of about 0.018 inches and the distal tip portion has a maximum outer diameter of about 0.035 inches, tapering to a smaller size at its tip. The enlarged distal tip portion comprises a metal core and plastic adhered to the outside thereof. The enlarged tip portion is about 3 cm long. The guidewire body is coated with a lubricious coating.

In another aspect, the invention features a method for positioning a dilatation balloon catheter within an occlusion in a body lumen. The method includes providing a guidewire comprising an elongated main guidewire body of a small, first diameter, the guidewire terminated at its distal end with an enlarged tip portion having a lubricious outer surface shaped and constructed to penetrate the occlusion. The guidewire body is constructed to be relatively flexible in the distal end corresponding to the enlarged tip and relatively stiffer in portions proximal thereof for manipulation of the wire from its proximal end. The guidewire is manipulated in the body lumen in the proximity of the occlusion, maneuvering the enlarged tapered tip portion across the occlusion, the tip portion creating a enlarged passageway in the occlusion. The dilatation balloon catheter is advanced over the guidewire body into the passageway in position for dilatation of the occlusion, the balloon catheter having a predetermined outer diameter of about the same maximum size as the tip portion of the guidewire.

Preferred embodiments include providing the guidewire with an outer sleeve having a lumen sized to slide over the main body of the guidewire and butt against the enlarged tip portion, the sleeve when slid over the main body contributing to the axial stiffness of the combination to enable manipulation through the occlusion and removing the outer sleeve member after the step of manipulating the tip portion across the occlusion and before the step of sliding the dilatation catheter along the guidewire. The body lumen is preferably an occluded coronary artery. The guidewire body and enlarged tip are constructed cooperatively, such that the distal end of the guidewire corresponding to the enlarged member has greater flexibility at distal portions than proximal portions.

DESCRIPTION OF THE PREFERRED EMBODIMENTS

We briefly describe the drawings.

BRIEF DESCRIPTION OF THE FIGURES

FIG. 1 is a cross section of a guidewire having an enlarged lubricious tip according to the present invention.

FIG. 2 is an axial cross section of the enlarged lubricious tip taken along line 2—2 of FIG. 1.

FIG. 2a is an enlarged section view of the lubricious coating of the tip of the guidewire of FIG. 2.

STRUCTURE

Figure 3:
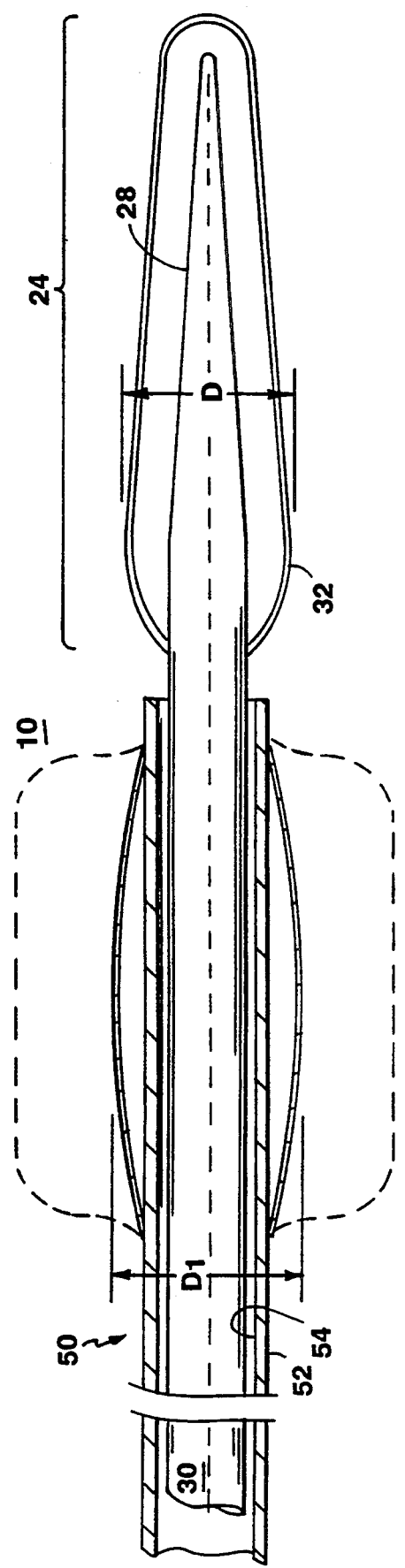
FIG. 3 is a cross section of a dilatation balloon catheter slid over the guidewire of FIG. 1.

Referring to FIG. 1, the guidewire 10 of the invention for particular use in coronary blood vessels has an elongated main wire body 20 and an enlarged distal end portion 24 that has a lubricious outer surface. The elongated wire body 20 is formed of a solid core superelastic alloy, such as Nitinol, or alternatively it is made of a linear elastic material such as titanium, tantalum, stainless steel. In an alternative embodiment, the guidewire is a hollow material, e.g., a superelastic alloy. In the embodiment of FIG. 1, of particular use in small blood vessels, the wire has a diameter, d, of 0.018". A continuation 28 of the wire body at the distal end smoothly tapers along a length T, e.g., 2 cm, from the diameter of the main body, i.e., 0.018" to a distal tip 29 having a diameter $d_1$, e.g., 0.003" to 0.005". This tapered continuation serves as a core of the enlarged distal portion 24. In combination with the outer covering 22 it defines a distal tip region of relatively greater flexibility than the main body, providing a guidewire that smoothly becomes more flexible in the direction of the tip.

Referring to FIG. 1, the enlarged portion 24, extends proximally a limited distance C, e.g., 3 cm, over the tapered core portion 28. As shown in FIG. 1, the covering 22 covers the entire length of the tapered core 28 and partially extends over the main body 26. The enlarged covering 22 is generally axisymmetric with respect to wire axis 30 and has a maximum diameter D of 0.035" at a point 32 located over three-fourths of the distance C from the distal tip. From its maximum diameter, the enlarged covering 22 tapers to a rounded point 38 at its distal end 36 to facilitate penetration into and movement through an occlusion. This taper enables the progressive enlargement of a passage through the occlusion as the guidewire advances. The enlarged covering 22 also smoothly tapers at a greater rate proximally from its maximum diameter to the main body of the guidewire 20 at the proximal end 34, this taper preventing the enlarged portion from snagging upon withdrawal of the guidewire. In particular embodiments, the taper length T may be approximately 10 cm to allow a gradual transition in flexibility from body to tip. The tip of the enlarged portion is preferably curved or angled. In preferred embodiments, the curve 31 is an arc of approximately 60° with a radius of about 0.25". The shape of the tip 29 e.g. the curvature, which causes a deflection of the wire when it encounters objects in the lumen, along with the enlarged nature of the tip, allows the wire to be urged forward with reduced chance that the guidewire will perforate the artery. It will be understood that the taper may begin at a point proximal to or distal from the proximal edge of the enlarged tip and further the taper may be of other desired lengths, e.g., 30 cm.

Referring to FIGS. 1 and 2, the covering 22 consists of a main layer 40 and a thin hydrophilic, lubricious outer layer 42. The main layer 40 can be made of a low-density, very flexible material such as a polyurethane or EVA (ethylene vinyl acetate), nylon, polyethylene, or PET and can be formed on the distal end of guidewire core 20 by extrusion, dipping or shrink formation. In the embodiment described, the main layer 40 is very flexible relative to the tapered core 28, and adds little mechanical strength to the combination (i.e., the mechanical characteristics of the guidewire core dominate the mechanical characteristics of the enlarged distal portion). The thin, lubricious outer layer 42 is formed of a low coefficient of friction, e.g., hydrophilic, material bonded to the main layer 40. In the figures, the relative thickness of the lubricious outer layer 42, which is typically less than 0.003" (dry thickness), is greatly exaggerated for clarity. Suitable materials are disclosed in "Lubricious Antithrombogenic Catheters, Guidewires and Coatings", U.S. Pat. No. 5,135,516, the contents of which are incorporated herein by reference.

As described in the above-referenced U.S. Pat. No. 5,135,516, the lubricious coating 42 can be a hydrogel, a polymer which is hydrated in the presence of water, and swollen such that a hydrated film contains a greater percentage of water by weight than polymer. This unique property reduces the surface friction of the polymer, creating a "super-slippery" surface that enhances the ability of the device to cross an occlusion. Preferably the coefficient of friction is 0.02-0.6. The thickness of the lubricious outer surface 42 may swell considerably when it is hydrated. Since only the thin coating is swellable, however, and the inner portions of the tip are made of dimensionally stable material, the dimensions of the tip are substantially maintained.

In particular in the above-referenced U.S. Pat. No. 5,135,516, when dry, the coating is preferably of the order of about 1.0 to 10 $\mu$m thick, a 2 to 5 $\mu$m coating is typical, although very thin coatings, e.g., of about 0.2-0.3 $\mu$m (dry) and much thicker coatings (e.g. more than 10 $\mu$m dry) are also possible. As shown in enlarged cross-section view, FIG. 2a, the coating 42 includes a lubricious binding component, shown schematically as 43, and an optional antithrombogenic component, shown schematically as 44. The binding component 43 is a hydrophilic, swellable highly lubricious polymer layer having carboxyl groups (acid groups) with quaternary ammonium cations bonded into the polymer layer. The binding layer 43 acts to bind both the coating to the surface the antithrombogenic component 44 to the coating.

The antithrombogenic component 44 is an antithrombogenic anion, for example, heparin, which is electrostatically attracted to the quaternary ammonium cations of the binding layer in a manner allowing time release of heparin to inhibit clot formation.

In a particular method of forming the coating, the binding component of the thin film is formed on the main layer 40. A lubricious, hydrophilic, water-swellable, acid-containing polymer, for example, polyacrylic acid, is reacted with the binding component. A quaternary ammonium salt, for example a quaternary ammonium halide salt, is then applied to the polymer acid surface to neutralize acid moieties of the polyacrylic acid polymer. The surface is then dried and, if desired, heparin is applied to the surface.

Other suitable polymer coatings are discussed in "Medical Instrument and Method For Making," European Patent Application 0 166 998, by Terumo Corporation, having a reactive functional group covalently bonded with a water-soluble polymer or derivative thereof, such as a cellulosic polymer, maleic anhydride polymer, polyacrylamide, or water-soluble nylon. However, the lubricious coating is not necessarily hydrophilic. A thin coating of other suitable materials having a low coefficient of friction might also be used, e.g., polyurethane, polyethylene, nylon, or a PET or EVA material. In alternative embodiments the wire body is also coated with a lubricious material. The coating also enhances insertion, such as into an outer tube or into a catheter shaft. It will also be understood that drugs such as antiproliferatives may be incorporated into suitable polymer coatings.

The guidewire 10 may be used in combination with an angioplasty balloon catheter 50 as shown in FIG. 3. The balloon catheter 50 consists of a catheter body 52 having an internal lumen 54 sized to allow the catheter body to slide along the length of guidewire main body 26. An angioplasty balloon 56, shown here in its deflated condition, is disposed near the distal end of the catheter 50. The outer diameter $D_1$ of the deflated balloon 56 generally corresponds to the maximum diameter D of the enlarged distal end portion 24 of the guidewire. When in dilatation position, the balloon 56 is inflated by passing a fluid through the lumen 54 of the catheter body. Once inflated, as shown as the dotted line, the balloon becomes larger, as determined by preselection of the balloon size.

The invention is suited for the treatment of various occluded ducts and vessels, such as blood vessels. The dimensions of the guidewire and other portions of the invention are varied according to the dimensions of the duct or vessel to be treated. For example, a large femoral artery or a large duct requires a relatively large guidewire and tip.

Figure 4:
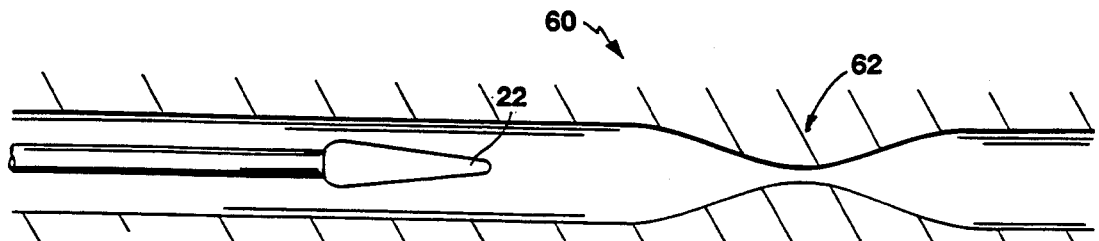
FIGS. 4–4b are schematic views of a guidewire having an enlarged lubricious tip of the present invention positioned in a body lumen.
Figure 4A:
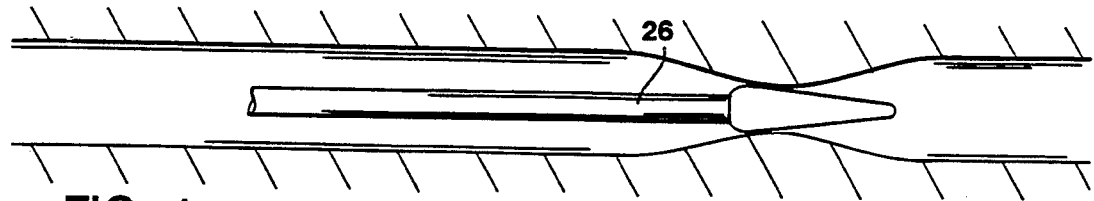
FIGS. 4c–4d show a dilatation catheter positioned over the guidewire.
Figure 4B:
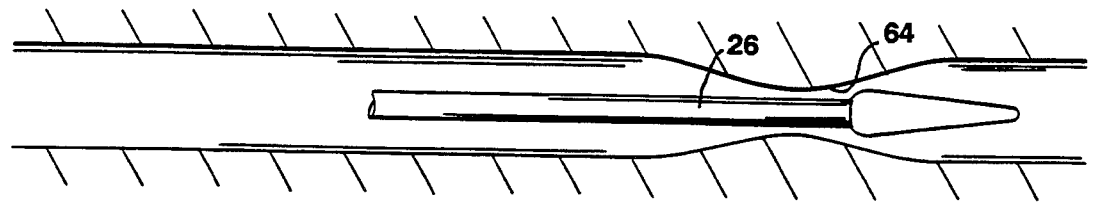
Figure 4C:
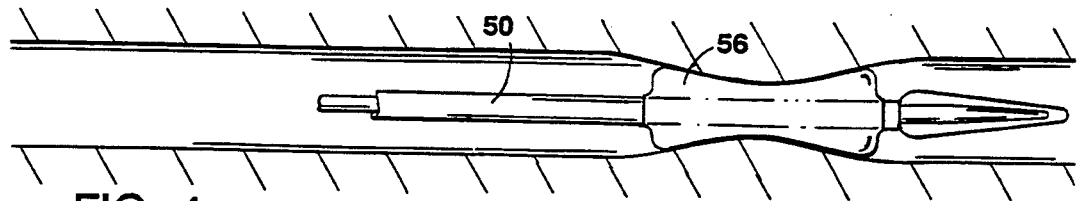
Figure 4D:
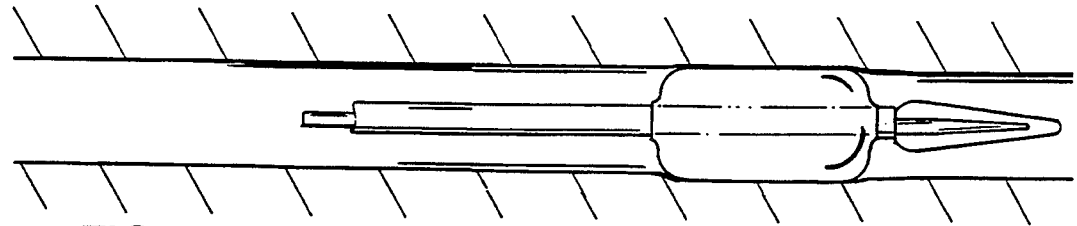

The guidewire 10 is especially suited for the treatment of vascular ailments, such as dilatation of a vascular occlusion in a small blood vessel, in particular a coronary artery. Referring to FIG. 4, the distal end of the guidewire is inserted and positioned in coronary artery 60, using standard guidewire positioning procedures as known in the art. As shown in FIG. 4 the guidewire confronts an occlusion 62 of the coronary artery. Application of axial pressure on the proximal end of the guidewire advances the distal end of the guidewire and the enlarged lubricious end portion 24 to the occlusion site. Further axial pressure causes the lubricious end portion 24 to penetrate the occlusion 62 (FIG. 4a) by gradually and gently widening the occlusion and eventually cross occlusion 62 (FIG. 4b). Typically, the user rotates the wire as it is urged forward. Once the guidewire has crossed the occlusion 62, only the smaller diameter main body of the guidewire resides in the newly formed perforation or passage in the occlusion. The angioplasty balloon catheter 50 is then slid over the guidewire from the proximal end, and guided into the passage through the occlusion. Because the diameter of the deflated balloon 56 is approximately the same as that of the enlarged distal portion of the guidewire, the distal end of the ballon catheter fits in the perforation 64 made by the guidewire (FIG. 4c). Once positioned in the occlusion, the angioplasty balloon 56 can be inflated in normal fashion (FIG. 4d) until the occlusion is fully opened, at which time the catheter and guidewire can be withdrawn as a unit. If, however, the passage is not completely opened by the fully inflated balloon, the dilatation balloon catheter can be removed and a larger dilatation balloon inserted using the in-place guidewire. It will be appreciated that the enlarged portion of the guidewire, once inserted in the blood vessel and pushed past the occlusion, will not need to be removed before the dilatation is completed.

The wire core and enlarged member are cooperatively constructed to facilitate passage of the guidewire through a portion of a body lumen narrowed by disease, e.g., a blood vessel narrowed by plaque. The guidewire is of sufficient strength and flexibility to avoid kinking and enable good torque control as the wire is passed through tortuous lumens and urged against an occluded area by axial force from the proximal end, while the enlarged tip, which minimizes the likelihood that the guidewire could perforate the lumen wall, is of the proper resiliency and slipperiness to facilitate passage, e.g., by a gradual enlargement of the occluded area. The performance of the guidewire is selected by coordination of the flexibility and strength contributed by the guidewire and tip and the slipperiness of the tip. The guidewire is constructed to be relatively flexible in the distal end corresponding to the enlarged tip and relatively stiffer in portions proximal thereof. The guidewire and the tip may be tapered or of constant diameter. Preferably the end corresponding to the tip has gradually increasing flexibility from proximal portions to distal portions.

Figure 5:
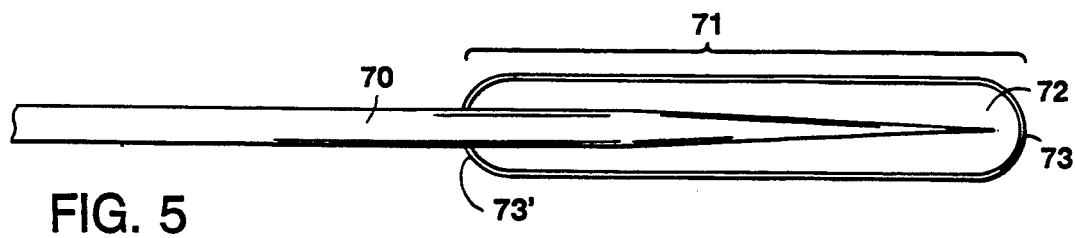
FIG. 5 is a cross section of an alternative embodiment of the guidewire having an enlarged lubricious tip of constant outer diameter and a tapered core.

Referring to FIG. 5, another embodiment of the invention is shown where the enlarged tip 71 has a generally cylindrical cross sectional configuration, with a constant outer diameter and rounded ends 73, 73'. The guidewire 70 is tapered at its distal end. As a result, the amount of material 72 increases distally in proportion to the decrease in the diameter of the inner core 70. Thus, the flexibility of the enlarged tip 71 increases in the distal direction.

Figure 6:
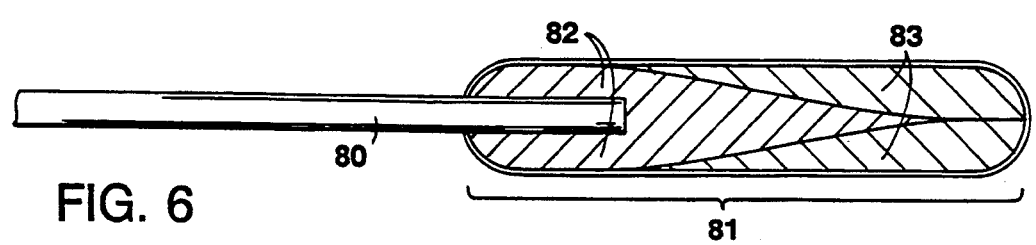
FIG. 6 is a cross section of an alternative embodiment of the guidewire having an enlarged lubricious tip of constant outer diameter and a core of constant diameter, the tip being increasingly flexible from its proximal end to its distal end due to the configuration of the material comprising the tip.

Referring to FIG. 6, another embodiment of the invention is shown where the guidewire 80 has a constant diameter and the enlarged lubricious tip 81 also has a constant outer diameter. The increasing flexibility from the proximal end to the distal end is due to the configuration of the material in the tip 81. In the embodiment shown, the enlarged tip 81 is comprised of two materials. A tear-shaped configuration 82 of high density polyethylene or of a PET substance tapers distally to a point, while the tapering portion of the tear-shaped configuration 82 is covered with distally increasing amounts of a soft or low-density polyethylene or of an EVA material 83.

Figure 7:
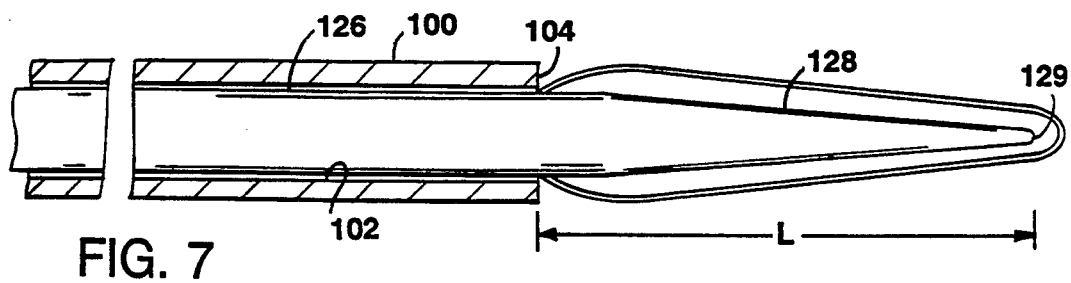
FIG. 7 is a cross section of a guidewire having an enlarged lubricious tip of the present invention having an outer sleeve for added axial stiffness.

Referring to FIG. 7, another embodiment of the invention is shown where a hollow outer sleeve 100 is combined with the guidewire to confer added stiffness to the guidewire. Prior to entry into the body, to enhance the guidewire's pushability and torquability, a thin stiff sleeve 100, (such as a cross wound multifilar tube, e.g. a Cragg wire TM, (available from Boston Scientific Corp., Watertown, Mass.)) is slid over the core 126 of the guidewire. The distal end 104 of the sleeve 100 is positioned a distance L, e.g., 8 cm, from the distal end 129 of the tapered core 128 to provide differential stiffness to the guidewire in its distal region. The sleeve and guidewire are positioned as a unit in the occluded blood vessel, and after the guidewire and sleeve have crossed the occlusion and are in a position analogous to FIG. 4b, the connection at the proximal ends is undone and the hollow outer sleeve is removed, leaving the guidewire in position to accept an angioplasty balloon catheter as described above. In alternative embodiments, the outer sleeve is made from a stiff plastic, such as polyimide, or a superelastic alloy.

Figure 8:
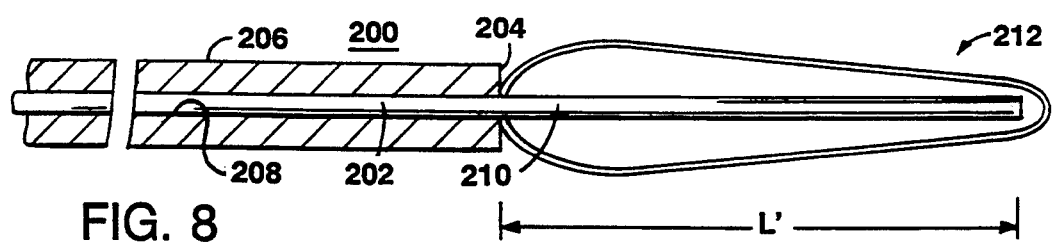
FIG. 8 is a cross section of an alternative embodiment of the guidewire having an enlarged lubricious tip of the present invention.

Referring now to FIG. 8, another embodiment of the invention is shown where the main body of the guidewire 200 comprises an internal wire 202 within an outer sleeve member 206. An extension of the wire core 202 extends distally a length L' (e.g., 3–10 cm) from the distal end 204 of the outer sleeve member 206. The core 202 is formed of a superelastic alloy, such as Nitinol, and the extension of the core into an enlarged end portion 212 has a uniform diameter (e.g., no substantial taper) of 0.005" over its length. The outer sleeve member 206 is formed from a thin-walled hypodermic tube having an outer diameter of 0.018". The internal lumen 208 of the sleeve member has an internal diameter equal to the outer diameter of internal core 202 and is fixedly attached to the outer surface of the internal core 202. The enlarged covering 212 is tapered with a lubricious surface provided on the distal end portion 210 of the internal core in the manner described above. The lubricious covering, as described above, is very flexible so that the mechanical properties of the internal core 202 dominate the properties of the distal tip portion 210 of the guidewire.

Figure 9:
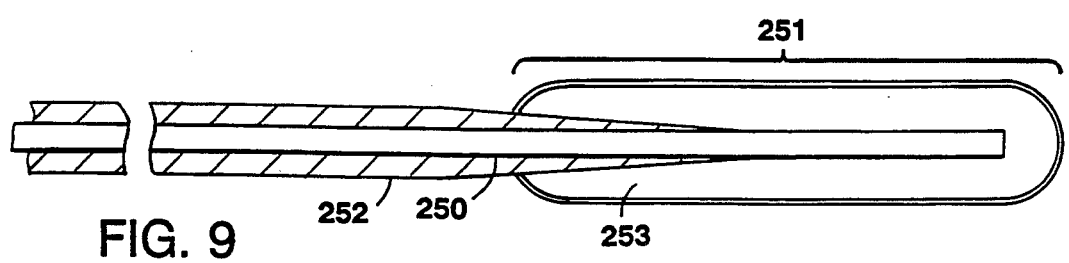
FIG. 9 is a cross section of an alternative embodiment of the guidewire having an inner core of constant diameter, an enlarged lubricious tip of constant outer diameter, and an outer sleeve tapered at its distal end.

Referring to FIG. 9, another embodiment of the invention is shown where the guidewire 250 has a constant diameter and the enlarged lubricious tip 251 has a constant outer diameter. In this embodiment, however, the fixed outer sleeve 252 tapers toward its distal end, which extends partly into the enlarged tip 251. The amount of lubricious material 253, therefore, distally increases to provide distally increasing flexibility. In preferred embodiments, the taper length is approximately 10 cm to achieve a gradual transition from the stiff body to the flexible tip.

Figure 10:
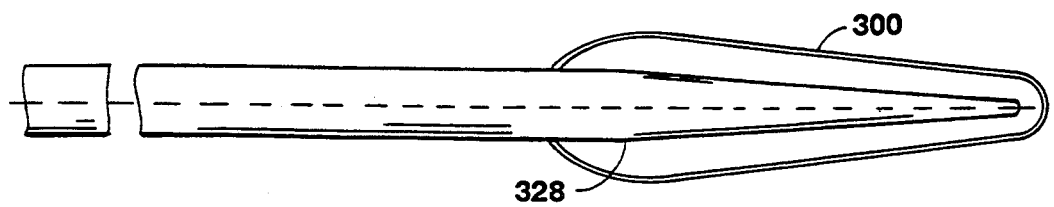
FIG. 10 is a cross section of an alternative embodiment of the guidewire having a tapered, enlarged lubricious tip of the present invention.

Referring to FIG. 10, another embodiment of the invention is shown where the guidewire has an enlarged lubricious tapered covering 300 as provided on the distal end portion 328 of the internal core in the manner described above. The lubricious tapered covering 300 is formed from a suitable elastomeric material alone, (e.g., polyurethane) and does not include an additional layer as discussed above in conjunction with the embodiment in FIG. 1.

Figure 11:
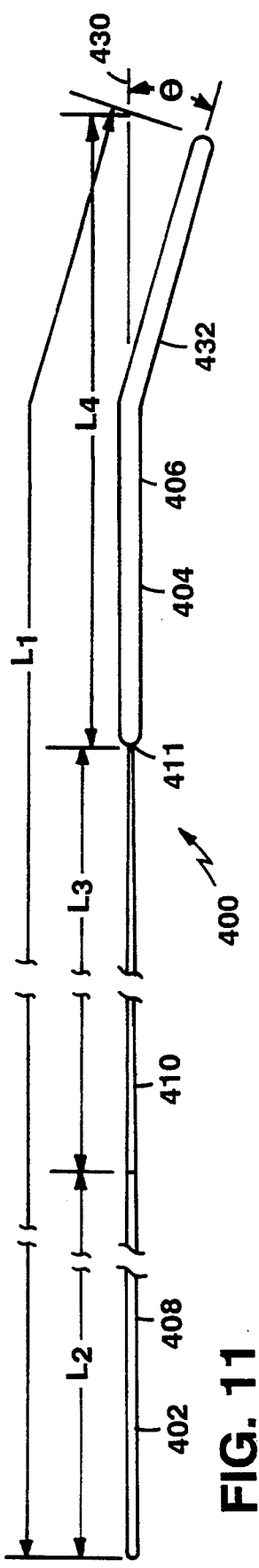
FIG. 11 is a side view of an alternative embodiment of a guidewire.
Figure 11A:
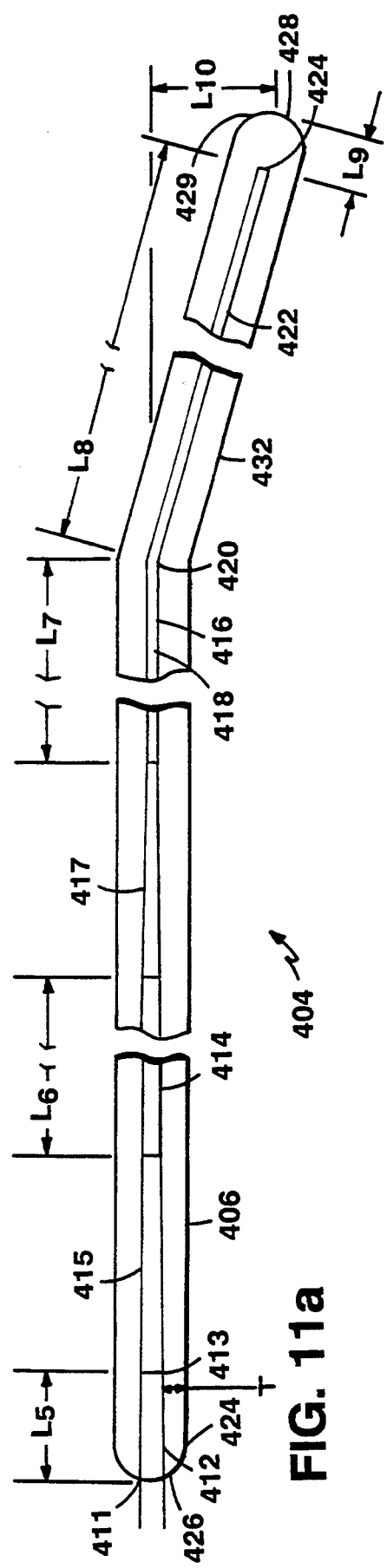
FIG. 11a is a cross section of the enlarged distal end of the wire in FIG. 11.

Referring to FIGS. 11 and 11a, another embodiment of the invention is shown. The wire 400, configured particularly for use in coronary arteries, has an overall length $L_1$, about 300 cm, including an elongated wire body 402 and an enlarged distal end portion 404 with a soft outer polymeric element 406. The wire body is preferably formed of metal, e.g., a superelastic nitinol. The wire body includes a proximal portion 408 of constant diameter, about 0.016 inch, and length, $L_2$, about 270 cm, followed by a taper portion 410 tapering distally over a length $L_3$, about 30 cm to a smaller diameter, about 0.0070 inch, at a position 411 just proximal of the enlarged distal end portion 404.

The enlarged distal end portion 404 extends an axial length, $L_4$, about 2.0-3.0 cm, typically about 2.2 cm, and is a composite of an extension of the wire 402 and the surrounding enlarged soft polymeric member 406. The taper of the wire in taper portion 410 continues within the enlarged distal end portion, taper portion 412, over a length, $L_5$, about 0.25 cm, to a diameter slightly less than 0.007 inch at position 413 at the distal end of portion 412. The taper portion 412 is followed (after a short (about 1.5 mm), tapered step 415) by constant diameter portion 414 of length $L_6$, about 0.6 cm, and diameter about 0.006 inch, which is followed (also after a short (about 1.5 mm) step 417) by a second constant diameter portion 416 with a diameter of about 0.004 inch. The constant diameter portion 416 has a first region 418, extending a length $L_7$, about 0.6 cm, to a bend 420, and a second region 422 of length, $L_8$, about 1.0 cm, to the distal end 424 of the wire.

The soft outer polymeric element 406 has a length, $L_4$ about 2.2 cm, and extends, $L_9$, about 2-4 mm from the distal end 424 of the wire body. The extension of the polymer beyond the distal end 424 of the wire is sufficient to form a soft distal tip but short enough to allow the polymer to follow the direction formed by the bend in the wire and to avoid buckling. The proximal end 426 of the polymeric element is gently tapered over a length of about 1-1.5 mm from the position 411 of the wire body just proximal of the enlarged distal end, to a maximum diameter region 427 of about 0.025 inch. The distal end 428 of the element 406 is curved or rounded. The polymeric element is substantially of constant diameter, but tapers slightly from the maximum diameter region 427 toward the distal end, reducing the diameter of the element 406 at the region 429, just proximal of the rounded end 426, by about 0.002 inch.

The soft outer polymeric element 406 is formed of a soft polymer of sufficiently low durometer, for example, 35 "shore D" or less, such that the mechanical characteristics of the wire dominate the mechanical characteristics of the enlarged distal end portion. The polymeric element preferably does not substantially increase the stiffness of the enlarged distal end, even at the small diameter portions 412, 414, 416 of the wire body. The polymer is, for example, a low density, nylon-like, polyether block amide (PEBA) that has a durometer of around 25 "shore D" (e.g. Pebax 25-335A000, density around 1.02 g/cc, Atochem, North America, Inc., Philadelphia, Pa.). Preferably, the bending flexibility of the portion 414 of the wire body is reduced by less than 10 percent, typically less than 5 percent, by the presence of the enlarged polymeric element as measured by pushing the end of the wire against a load cell (Instron) and measuring force until deflection. As illustrated, the soft, low durometer, low mechanical strength nature of the polymer enables the polymeric element to follow the bend of the wire within to form an enlarged distal end portion with a deflected portion 432. (In this embodiment, the polymer itself is not permanently set in the form of the bend.)

The thickness (T) of the polymer is approximately equal to (e.g. about 80%) or greater than the radius of the wire it overlies. In this example, in the region 427, the polymer thickness is about 0.009 inch, where the wire radius is about 0.0035 inch. In more distal regions of the enlarged distal end, corresponding to wire portions 414, 416 the ratio of polymer thickness to wire diameter increases as the outer diameter of the enlarged distal end remains substantially constant and the diameter of the wire decreases. The polymeric element may include tungsten powder within the polymer matrix to enhance radiopacity.

The guidewire 400 features a gentle bend in the enlarged distal end portion, creating deflected portion 432, sufficient to aid steering the wire into a desired lumen within a body by rotation of the wire, but not so great as to substantially impede the ability of the wire to cross an occlusion, i.e., the wire remains axially pushable so that it does not excessively buckle or prolapse as it is urged against a narrowed region of the lumen. The bend must also be not so large as to cause a scraping along the lumen wall in occluded regions, which could loosen plaque or the like coating the wall and forming the occlusion. Preferably the bend is positioned about 0.5-0.75 cm from the distal end 428 of enlarged distal portion 406 and is at an angle, $\theta$, of about 10°-35° from the wire body axis 430, creating a deflection length, $L_{10}$, of about 0.26 cm. In a particular embodiment, the bend angle $\theta$ is about 15°, and the bend is positioned about 0.75 cm from the distal end 428. In another embodiment, the angle $\theta$ is about 30° and the bend is about 0.5 cm from the distal end 128. Larger angles and/or bend positions further from the distal end and hence, larger deflection lengths and bending moments, might be used in embodiments where the enlarged distal portion is made stiffer, to prevent prolapse, such as by using a larger diameter wire or stiffer polymer for the polymeric element.

A guidewire for crossing occlusions as described in FIGS. 11-11a may be constructed by procuring a wire, e.g. a superelastic nitinol, having the length and diameter profile described above (U.S. Nitinol Saratoga, Calif.). (The short steps 415, 417 may be a result of the grinding process, and provide a transition of stiffness and strength in the portions of different diameter.) The polymer used in the enlarged soft polymeric element (Pebax, supra) is compounded at 80 percent tungsten by weight (microfine tungsten particles, 1-5 microns) and extruded into a continuous straight tube which is cut in lengths of about 2 cm. The distal end of the guidewire body is dipped in a urethane primer (A1104 Primer, B. F. Goodrich, Cleveland, Ohio) for about 15–20 seconds to form a thin coat. The primed distal end is then dipped in a urethane adhesive (Estame 5701, B. F. Goodrich, Cleveland, Ohio). The polymer tube is slid over the distal end of the wire such that it extends beyond the wire by about 1 mm. A silicon tubing is placed over the polymer tube and the distal end heated at about 350° F. for about 60 seconds which attaches the polymer tube to the wire and at the same time, causes the polymer tube to taper slightly to the distal end and seals the distal end of the tubing extending beyond the core. The silicone outer tube is then removed and the distal end of the polymeric element buffed to form a rounded curved end. The tip of the wire is then bent at a desired location from the distal end and a desired angle, as discussed above. A lubricious, hydrophilic coating as discussed previously is then applied to the outer surface of the polymeric element and a silicone coat provided on a 140 cm length of the exposed wire running proximally from about 1 cm proximal of the enlarged distal portion.

Other embodiments are possible. For example, the wire may include a preset bend when using nitinol as the wire body material or as indicated, or, in other embodiments, the wire may be configured to facilitate making the bend just prior to use by the physician by using a nonsuperelastic wire, particularly a precursor of a superelastic which has improved flexibility over non-superelastics and, at the same time, takes a set more easily than superelastics. Wires of this latter type are discussed in copending U.S. application Ser. No. 07/954,469, filed Sep. 30, 1992, the entire contents of which is hereby incorporated by reference. The bend of the distal end of the wire may also take on other forms, such as a J-tip. Regions of the wire can be engineered for desired results. For example, the portion of the wire just proximal of the enlarged distal portion might be made a slightly larger diameter, e.g. about 0.008 or 0.009 inch in the embodiment of FIG. 11, to enhance strength and stiffness in this area. The polymeric material may be a low density foam. The wires can be sized for particular vascular uses including the peripheral vascular or neurovascular regions. The wires can also be used in nonvascular applications. For example, the guidewire may be constructed and dimensioned for use in various vessels such as the ureter, urethra and bile ducts.

Numerous other embodiments are within the spirit and scope of the invention and the following claims:

We claim:

1. A steerable medical guidewire for gently penetrating an occlusion within a vessel comprising:
    an elongated main guidewire body defining a longitudinal axis and having selected stiffness characteristics along its length to allow the guidewire to be urged through a narrow, tortuous body lumen by application of forces at a proximal end,
    the guidewire having a composite enlarged distal end portion comprised of an extension of said main guidewire body and a surrounding enlarged soft outer polymeric element, said polymeric element having a substantial thickness compared to corresponding portions of said guidewire body, said outer polymeric element having a lubricious outer surface,
    said enlarged distal end portion including a gently deflected region, to enable steering of said guidewire inside said vessel,
    said deflected region and the stiffness of said guidewire cooperatively constructed to permit said enlarged distal end portion, including said deflected portion, to gently penetrate said occlusion and form a passage therein.

2. The steerable guidewire of claim 1 wherein said deflected portion is formed by at an angle of about 15° to 35° from the longitudinal axis of said main guidewire body.

3. The steerable guidewire of claim 2 wherein said angle is formed by a bend located about 0.5 to 0.75 cm from the distal end of the polymeric element.

4. The steerable guidewire of claim 3 wherein said enlarged distal end portion is a composite of an extension of said main guidewire body and a surrounding enlarged soft outer polymeric element having a diameter larger than the diameter of portions of said main guidewire body proximal of said enlarged distal end portion, the portion of said guidewire body in the distal part of said enlarged distal end portion being of smaller diameter than the portion of said guidewire body in the proximal part of said enlarged distal end portion, the flexibility of said enlarged distal end portion being determined over substantially all of its length predominantly by the respective portions of the guidewire body therewithin.

5. The steerable guidewire of claim 4 wherein said guidewire is adapted for use in the vascular system and has a wire body with a maximum diameter of about 0.018 inch or less.

6. The steerable guidewire of claim 5 wherein said enlarged distal end portion has a diameter of about 0.035 inch or less.

7. The guidewire of claim 1 or 4 wherein, in at least portions of the enlarged distal end portion, the thickness of said soft polymeric element is about equal to or greater than the radius of the corresponding portion of the wire body.

8. The guidewire of claim 1 wherein said guidewire body is formed of a solid wire.

9. The guidewire of claim 8 wherein said guidewire body is nitinol.

10. The guidewire of claim 1 wherein the distal extremity of said extension of said main guidewire body is about 0.003 to about 0.005 inch diameter.

11. The guidewire of claim 1 wherein said polymeric element has a substantially cylindrical configuration of substantially constant cross-sectional diameter and a rounded distal end.

12. The guidewire of claim 1 wherein said soft outer polymeric element is formed of a flexible nylon polymer.

13. The guidewire of claim 1 wherein the exterior surface of said soft outer polymeric element includes a thin hydrophilic coating of a hydrogel polymer.

14. The medical guidewire of claim 1 wherein said enlarged distal end portion is about 2 to 3 cm long.

15. The guidewire of claim 1 wherein said guidewire body has an exterior surface that includes a lubricious coating.

16. A steerable guidewire for gently penetrating an occlusion within a vessel comprising:
    an elongated solid main guidewire body having selected stiffness characteristics along its length to allow the guidewire to be urged through a narrow, tortuous body lumen by application of forces at a proximal end, and
    an enlarged distal end portion including a soft polymeric element having a substantial thickness compared to portions of the guidewire proximal thereof and a permanently deflected portion to enable steering of said guidewire.

* * * * *

UNITED STATES PATENT AND TRADEMARK OFFICE
CERTIFICATE OF CORRECTION

PATENT NO. : 5,385,152

DATED : January 31, 1995

INVENTOR(S) : John E. Abele et al.

It is certified that error appears in the above-indentified patent and that said Letters Patent is hereby corrected as shown below:

Col. 3, line 53, "a" should be --an--.

Col. 7, line 32, "ballon" should be --balloon--.

Signed and Sealed this

Thirtieth Day of April, 1996

Attest:

BRUCE LEHMAN

Attesting Officer

Commissioner of Patents and Trademarks